(12) United States Patent
Lee et al.

(10) Patent No.: US 9,220,480 B2
(45) Date of Patent: Dec. 29, 2015

(54) METHOD AND APPARATUS FOR PROVIDING MULTI SPECTRAL DOPPLER IMAGES

(75) Inventors: Sang-mok Lee, Gangwon-do (KR); Dong-gyu Hyoun, Gangwon-do (KR)

(73) Assignee: SAMSUNG MEDISION CO., LTD., Hongcheon-Gun, Gangwon-Do (KR)

( * ) Notice: Subject to any disclaimer, the term of this patent is extended or adjusted under 35 U.S.C. 154(b) by 707 days.

(21) Appl. No.: 13/482,567

(22) Filed: May 29, 2012

(65) Prior Publication Data

US 2013/0184578 A1 Jul. 18, 2013

(30) Foreign Application Priority Data

Jan. 16, 2012 (KR) ........................ 10-2012-0004910

(51) Int. Cl.
| | | |
|---|---|---|
| *A61B 8/00* | (2006.01) | |
| *A61B 8/08* | (2006.01) | |
| *A61B 8/06* | (2006.01) | |
| *G01S 7/52* | (2006.01) | |
| *G01S 15/89* | (2006.01) | |

(52) U.S. Cl.
CPC . *A61B 8/488* (2013.01); *A61B 8/06* (2013.01); *A61B 8/463* (2013.01); *A61B 8/466* (2013.01); *A61B 8/469* (2013.01); *A61B 8/483* (2013.01); *A61B 8/485* (2013.01); *G01S 7/52066* (2013.01); *G01S 15/8979* (2013.01)

(58) Field of Classification Search
USPC .......................................... 600/407, 437–43
See application file for complete search history.

(56) References Cited

U.S. PATENT DOCUMENTS

| | | | |
|---|---|---|---|
| 5,785,655 A | 7/1998 | Goodsell, Jr. et al. | |
| 8,353,835 B2 | 1/2013 | Kim et al. | |
| 2005/0096543 A1* | 5/2005 | Jackson et al. | 600/441 |
| 2007/0167790 A1 | 7/2007 | Kim et al. | |
| 2009/0066727 A1* | 3/2009 | Lu et al. | 345/643 |
| 2009/0264758 A1* | 10/2009 | Fujita et al. | 600/443 |
| 2012/0089024 A1 | 4/2012 | Hong | |

FOREIGN PATENT DOCUMENTS

| | | |
|---|---|---|
| JP | 10-225456 | 8/1998 |
| KR | 10-2008-0010031 A | 1/2008 |
| KR | 10-1097578 B1 | 12/2011 |
| WO | 0171376 A1 | 9/2001 |
| WO | 2007019216 A1 | 2/2007 |
| WO | 2011023797 A1 | 3/2011 |

OTHER PUBLICATIONS

Korean Office Action with English translation issued in KOrean Application No. 10-2012-0004910 dated Jun. 27, 2013.

(Continued)

*Primary Examiner* — Joel F Brutus
(74) *Attorney, Agent, or Firm* — McDermott Will & Emery LLP

(57) ABSTRACT

A method of providing multi spectral Doppler images, including displaying an ultrasound image of an object in a first region; setting a plurality of sample volumes in the displayed ultrasound image; obtaining a plurality of Doppler signals corresponding to the set plurality of sample volumes; and tridimensionally displaying in a second region the multi spectral Doppler images that are generated based on the obtained plurality of Doppler signals.

21 Claims, 10 Drawing Sheets

(56) References Cited

OTHER PUBLICATIONS

European Search Report issued in European Applicaiton No. 12162593.3 dated Apr. 15, 2013.

Korean Office Action, w/ English translation thereof, issued in Korean Patent Application No. KR 10-2012-0004910 dated Dec. 19, 2013.

* cited by examiner (a)  (b)

METHOD AND APPARATUS FOR PROVIDING MULTI SPECTRAL DOPPLER IMAGES

CROSS-REFERENCE TO RELATED PATENT APPLICATION

This application claims the benefit of Korean Patent Application No. 10-2012-0004910, filed on Jan. 16, 2012, in the Korean Intellectual Property Office, the disclosure of which is incorporated herein in its entirety by reference.

BACKGROUND OF THE INVENTION

1. Field of the Invention

The present invention relates to a method and apparatus for providing multi spectral Doppler images for effectively displaying multi spectral Doppler images in a single screen.

2. Description of the Related Art

An ultrasound diagnosis apparatus delivers an ultrasound signal from a body surface of a target object to a predetermined part in the body, and then obtains an image of tomography or hematocele of a soft tissue by using information of the ultrasound signal reflected from a tissue in the body.

The ultrasound diagnosis apparatus is advantageous in that it is small, is inexpensive, and displays in real-time. Also, the ultrasound diagnosis apparatus is not harmful such as radioactivity and thus is safe, so that it is widely used together with an X-ray diagnosis apparatus, a computerized tomography (CT) scanner, a magnetic resonance image (MRI) apparatus, a nuclear medicine diagnosis apparatus, and the like.

In general, an ultrasound diagnosis apparatus provides a brightness mode (B mode) image for indicating an amplitude of an ultrasound echo signal reflected from an object by using brightness, a Doppler mode image for indicating an image of a moving object in the form of spectrums based on a Doppler effect, a motion mode (M mode) image for indicating motion of an object at a predetermined position according to time, an elastic mode image for indicating a reaction difference between cases compression is applied to an object and compression is not applied to the object, and a color mode (C mode) image for indicating a speed of a moving object by using colors based on a Doppler effect, and the like.

SUMMARY OF THE INVENTION

According to an aspect of the present invention, there is provided a method of providing multi spectral Doppler images, the method including displaying an ultrasound image of an object in a first region; setting a plurality of sample volumes in the displayed ultrasound image; obtaining a plurality of Doppler signals corresponding to the set plurality of sample volumes; and tridimensionally displaying in a second region the multi spectral Doppler images that are generated based on the obtained plurality of Doppler signals.

The displaying may include displaying the multi spectral Doppler images in the form of a perspective view in a single graph.

The multi spectral Doppler images may include a plurality of vector Doppler images.

The method may further include setting colors corresponding to the set plurality of sample volumes; and applying the set colors to the multi spectral Doppler images and displaying the multi spectral Doppler images.

The method may further include further setting a sample volume to the displayed ultrasound image; and further and tridimensionally displaying a Doppler image corresponding to the further set sample volume in the second region.

The method may further include deleting a sample volume from the displayed ultrasound image; and deleting a Doppler image corresponding to the deleted sample volume from the second region.

The displaying may include rotating the multi spectral Doppler images by 360 degrees and displaying the multi spectral Doppler images.

The method may further include obtaining a cumulative Doppler image indicating a change in blood flow for a predetermined period of time corresponding to at least one sample volume from among a plurality of sample volumes; and displaying the obtained cumulative Doppler image in the second region.

The method may further include obtaining a first Doppler image at a first point of time corresponding to at least one sample volume from among the set plurality of sample volumes and a second Doppler image at a second point of time corresponding to the at least one sample volume; and tridimensionally displaying the obtained first Doppler image and the obtained second Doppler image in the second region.

The method may further include obtaining elastic data corresponding to the set plurality of sample volumes; and tridimensionally displaying in the second region a plurality of elastic images based on the obtained elastic data.

The method may further include obtaining an ultrasound echo signal corresponding to the set plurality of sample volumes; and tridimensionally displaying in the second region a plurality of motion mode (M mode) images based on the obtained ultrasound echo signal.

According to another aspect of the present invention, there is provided an apparatus for providing multi spectral Doppler images, the apparatus including an image processing unit for setting a plurality of sample volumes in a displayed ultrasound image; an obtaining unit for obtaining a plurality of Doppler signals corresponding to the set plurality of sample volumes; a display unit for displaying an ultrasound image of an object in a first region and tridimensionally displaying in a second region the multi spectral Doppler images that are generated based on the obtained plurality of Doppler signals; and a controller for controlling the image processing unit, the obtaining unit, and the display unit.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
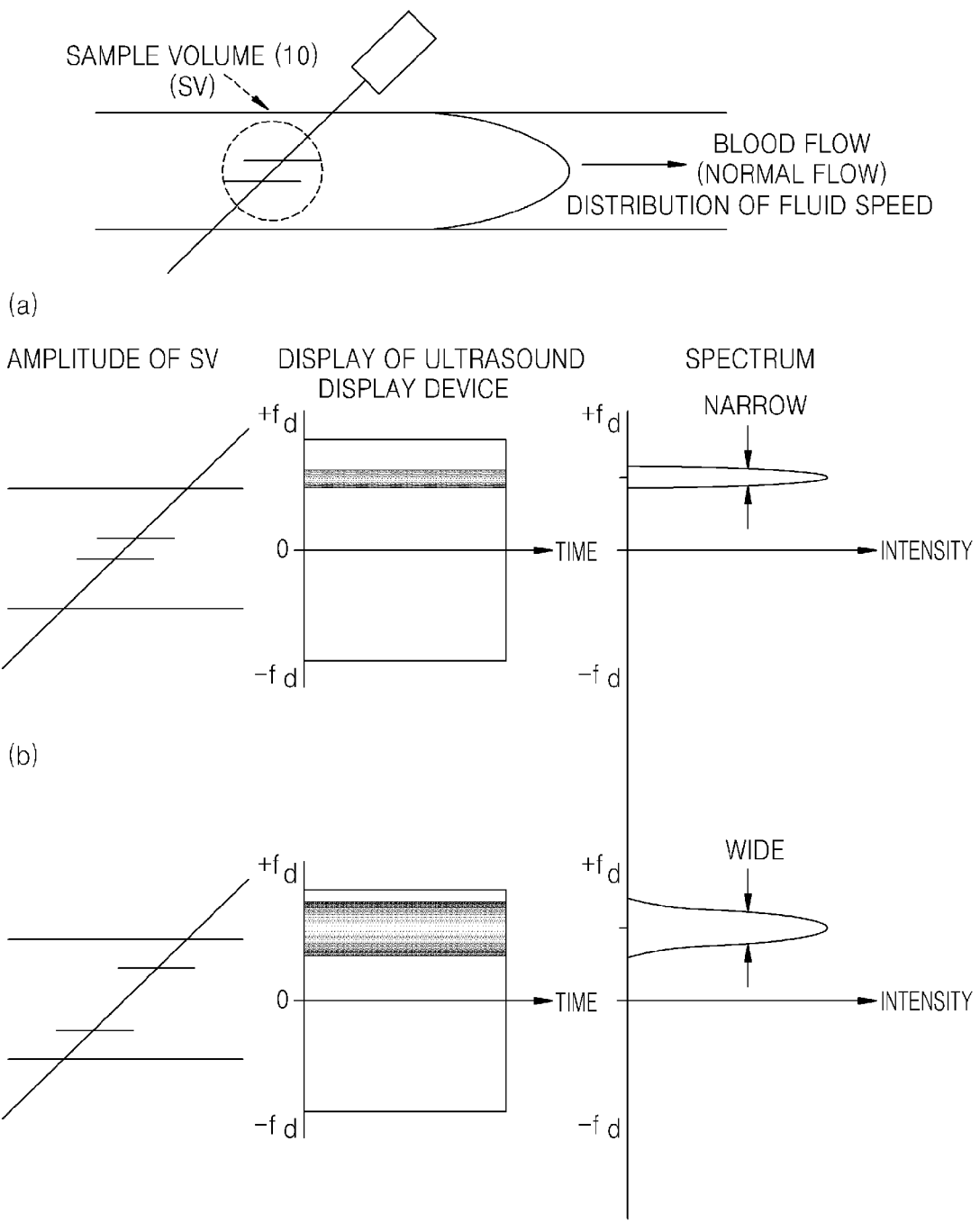
FIG. 1 is a diagram for explaining a sample volume of a general Doppler image.

Terms or words used in the following description should not be construed as being limited to common or general meanings but should be construed as fully satisfying the concept of the invention. In the following description, the applicant arbitrarily selects some terms or words, and in those cases, the detailed meaning are provided here.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

In the following description, "user" may indicate a medical expert including a doctor, a nurse, a clinical pathologist, a medical image expert, or the like but is not limited thereto.

Throughout the specification, the term "Doppler image" refers to an image that is obtained by receiving a Doppler signal from a moving object based on a Doppler effect and converting the received Doppler signal in the form of spectrum. According to an embodiment of the present invention, a Doppler image may be obtained by using at least one method of a continuous wave (CW) method, a pulsed wave (PW) method, a single gate method, a multigate method, and a color flow imaging method.

Hereinafter, the present invention will be described in detail by explaining exemplary embodiments of the invention with reference to the attached drawings. In the following description, functions or constructions that are not related to the present invention are omitted, and like reference numerals in the drawings denote like elements. Expressions such as "at least one of," when preceding a list of elements, modify the entire list of elements and do not modify the individual elements of the list.

FIG. 1 is a diagram for explaining a sample volume of a general Doppler image.

The sample volume refers to a limited area that receives a Doppler signal by using an operation of a range gate. A general ultrasonic apparatus may adjust the size of the sample volume by changing the size of a gate. As the size of the gate is increased, a volume for obtaining a Doppler signal is increased.

For example, when the sample volume is positioned in a central portion of blood vessel by using a narrow gate, a speed of blood flow may be obtained in a very narrow range, as shown in FIG. 1(*a*). On the other hand, when a wide gate is used, a speed of blood flow may be obtained in a wide range, as shown in FIG. 1(*b*).

According to an embodiment of the present invention, a user may select a plurality of sample volumes from an ultrasound image in order to obtain multi spectral Doppler images.

Figure 2:
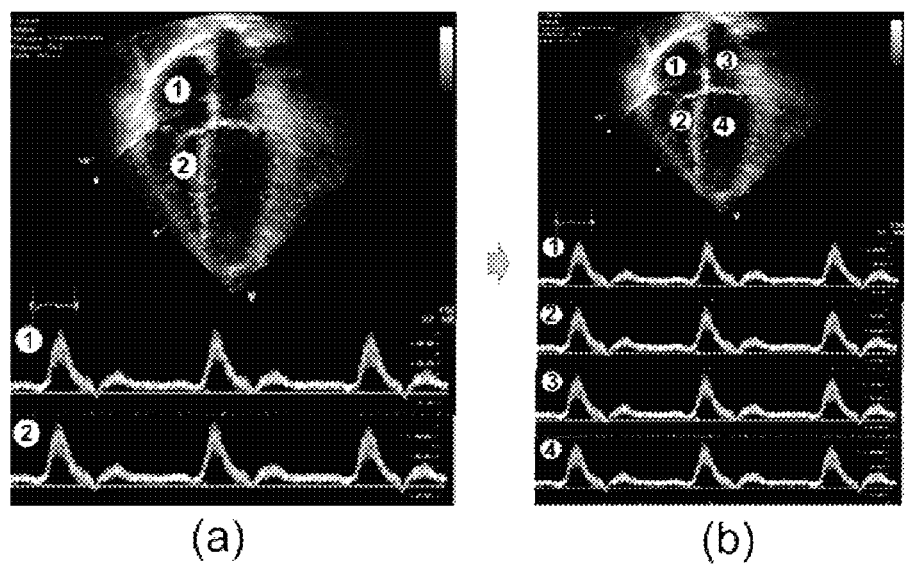
FIG. 2 is a set of images showing screens of a general ultrasound apparatus, on which a Doppler image is displayed.

FIG. 2 is a set of images showing screens of a general ultrasound apparatus, on which a Doppler image is displayed.

A general ultrasound apparatus may display a brightness mode (B mode) image and a Doppler image on a single screen. In this case, a general ultrasound apparatus may sequentially display Doppler images in the form of graphs below the B mode image. However, the number of Doppler images to be displayed on a screen is limited. In addition, as the number of the displayed Doppler image is increased, the size of the B mode image or the Doppler image is reduced.

For example, as shown in FIG. 2(*a*), when there are two sample volumes, Doppler images corresponding to the sample volumes are displayed in the form of graphs below the B mode image. However, as shown in FIG. 2(*b*), when the number of sample volumes is increased to four, since the number of Doppler images (graphs) displayed below the B mode image is increased to four, the sizes of the B mode image and the Doppler images are reduced.

Hereinafter, an apparatus for providing multi spectral Doppler images will be described in detail with reference to FIG. 3.

Figure 3:
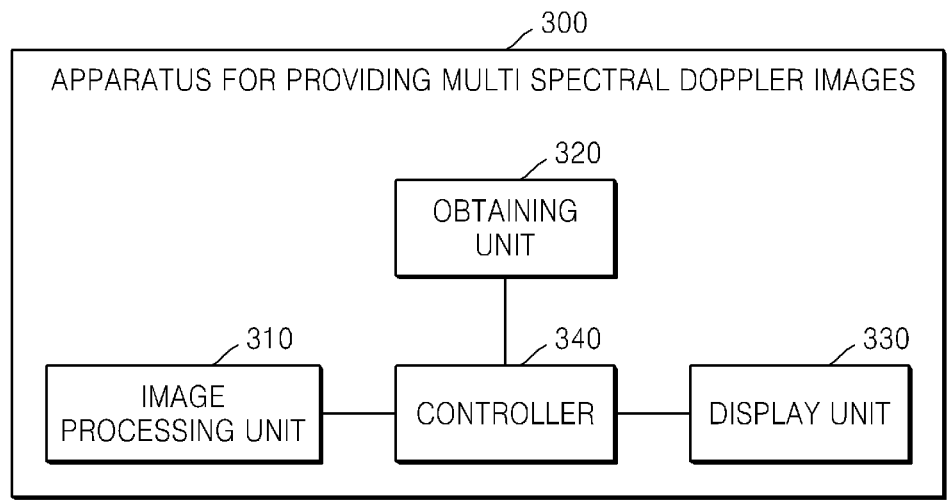
FIG. 3 is a block diagram of an apparatus for providing multi spectral Doppler images, according to an embodiment of the present invention.

FIG. 3 is a block diagram of an apparatus 300 for providing multi spectral Doppler images, according to an embodiment of the present invention.

The apparatus 300 according to the present embodiment refers to an apparatus for obtaining an ultrasound image or a Doppler image from an object by using ultrasound waves and displaying the obtained ultrasound image or Doppler image to a user.

The apparatus 300 according to the present embodiment may be embodied in various forms. For example, the apparatus 300 may be embodied in the form of fixed terminal or mobile terminal. Examples of the mobile terminal may include a laptop computer, a personal digital assistant (PDA), a tablet personal computer (PC), and the like.

As shown in FIG. 3, according to an embodiment of the present invention, the apparatus 300 may include an image processing unit 310, an obtaining unit 320, a display unit 330, and a controller 340. However, not all of the elements shown in FIG. 3 may be necessary. More elements than in FIG. 3 or less elements than in FIG. 3 may be included in the apparatus 300.

The image processing unit 310 may set a plurality of sample volumes in a displayed ultrasound image. In this case, according to an embodiment of the present invention, the image processing unit 310 may set a plurality of sample volumes based on a user's input.

According to an embodiment of the present invention, the ultrasound image may include a B mode image, motion mode (M mode) image, a color mode image, and an elastic mode image.

According to an embodiment of the present invention, the image processing unit 310 may set colors corresponding to the sample volumes. According to an embodiment of the present invention, the image processing unit 310 may set random colors corresponding to the sample volumes or may set colors corresponding to the sample volumes according to a user's input.

The image processing unit 310 may further set a sample volume in the displayed ultrasound image. In addition, the image processing unit 310 may delete a sample volume in the displayed ultrasound image.

The obtaining unit 320 may obtain an ultrasound image of the object. According to an embodiment of the present invention, the obtaining unit 320 may obtain the ultrasound image in a two-dimensional (2D) or three-dimensional (3D) form.

In addition, the obtaining unit 320 may obtain a plurality of Doppler signals corresponding to a plurality of sample volumes. According to an embodiment of the present invention, the obtaining unit 320 may transmit and receive an ultrasound signal for obtaining a Doppler signal of a region of interest in a pulse repetition frequency (PRF) to form a Doppler signal.

According to an embodiment of the present invention, the obtaining unit 320 may include a probe (not shown) for transmitting and receiving an ultrasound signal and a beamformer (not shown) for focusing transmission and receipt of ultrasound signals.

The obtaining unit 320 may obtain a cumulative Doppler image indicating a change in blood flow for a predetermined period of time corresponding to at least one sample volume from among a plurality of sample volumes.

The obtaining unit 320 may obtain multi spectral Doppler images with respect to which points of time for obtaining at least one sample volume from among corresponding sample volumes are different. For example, the obtaining unit 320 may obtain a first Doppler image with respect to which a point of time for obtaining a predetermined sample volume is a first point of time and then may obtain a second Doppler image with respect to which a point of time for obtaining the predetermined sample volume is a second point of time.

The obtaining unit 320 may obtain at least one of elastic data and an ultrasound echo signal, which correspond to a plurality of sample volumes. The elastic data may contain strain information of the object. The strain of the object refers to a degree of deformation of the object, which is caused by a force applied from the outside.

The display unit 330 may display information processed by the apparatus 300. For example, the display unit 330 may display an ultrasound image of the object on a first region. In addition, the display unit 330 may display multi spectral Doppler images in a second region. In this case, the display unit 330 may tridimensionally display multi spectral Doppler images in the second region.

According to an embodiment of the present invention, multi spectral Doppler images may be 3D Doppler images. Alternatively, multi spectral Doppler images may be vector Doppler images. According to an embodiment of the present invention, the vector Doppler image refers to a Doppler image indicating a directional component of a sample volume as well as a speed of the sample volume.

According to an embodiment of the present invention, the display unit 330 may display the multi spectral Doppler images along at least one axis in a single graph. For example, the display unit 330 may display multi spectral Doppler images along a horizontal axis in a single graph.

The display unit 330 may display multi spectral Doppler images corresponding to a plurality of sample volumes in the form of a perspective view in a single graph. According to an embodiment of the present invention, the display unit 330 may apply colors corresponding to the sample volumes to multi spectral Doppler images and may display the Doppler images.

When a sample volume is further set, the display unit 330 may further display a Doppler image corresponding to the sample volume along at least one axis in the single graph. On the other hand, when at least one sample volume is deleted from a plurality of sample volumes, the display unit 330 may delete a Doppler image corresponding to the deleted sample volume from the second region.

The display unit 330 may rotate multi spectral Doppler images by 360 degrees and may display the rotated Doppler images. In this case, a user may view the Doppler images from different points of view.

According to an embodiment of the present invention, the display unit 330 may display a cumulative Doppler image indicating a change in blood flow for a predetermined period of time corresponding to at least one sample volume from among a plurality of sample volumes.

The display unit 330 may tridimensionally display multi spectral Doppler images with respect to which points of time for obtaining a predetermined sample volume are different. In this case, the display unit 330 may display a first Doppler image with respect to which a first sample volume is obtained at a first point of time and a second Doppler image with respect to which the first sample volume is obtained at a second point of time in a horizontal axis direction in a single graph.

In the display unit 330, the first region for displaying the ultrasound image and the second region for displaying the Doppler image may be horizontally arranged or may be vertically arranged. According to an embodiment of the present invention, the display unit 330 may change the arrangement of the displayed ultrasound image and the displayed Doppler image according to a user's input.

In addition, the display unit 330 may adjust the size of the first region for displaying the ultrasound image and the size of the second region for displaying the Doppler region. For example, when a user wants to enlarge and view the ultrasound image, the display unit 330 may enlarge the first region for displaying the ultrasound image and may reduce the second region for displaying the Doppler image.

The display unit 330 may tridimensionally display in the second region a plurality of elastic images that are generated based on the elastic data. The elastic image (ACOUSTIC RADIATION FORCE IMPULSE IMAGING) refers to an image indicating the elasticity of an object. The elasticity of the object is related to histopathological change of the object. Tumor tissues are harder than normal tissues. That is, since the elasticity of tumor tissue is greater than the elasticity of normal tissue, when the same pressure is applied to the tumor tissue and the normal tissue, the strain of the normal tissue is greater than the strain of the tumor tissue. Thus, the elastic image may be used to diagnose tumor or cancer.

In addition, the display unit 330 may tridimensionally display in the second region a plurality of M mode regions that are generated based on the ultrasound echo signal. The M mode image is an image for indicating as brightness motions of organs by using ultrasound echo signals that are repeatedly obtained by a single fixed scan line.

When the display unit 330 and a touch pad are formed as a mutual layered structure to constitute a touch screen, the display unit 330 may be used as an input device as well as an output device. The display unit 330 may include at least one of a liquid crystal display, a thin film transistor-liquid crystal display, an organic light-emitting diode, a flexible display, and a 3D display.

The controller 340 may control overall operations of the image processing unit 310, the obtaining unit 320, and the display unit 330.

Figure 4:
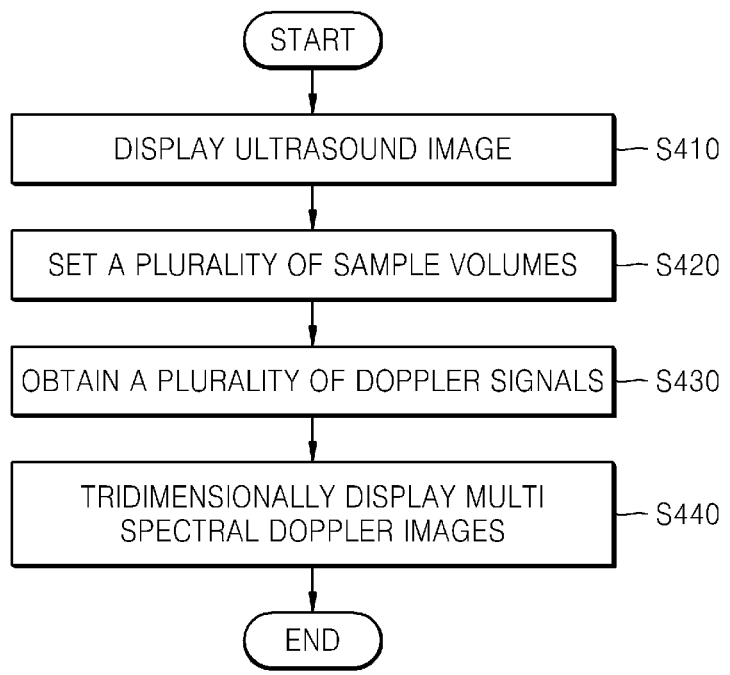
FIG. 4 is a flowchart of a method of providing multi spectral Doppler images, according to an embodiment of the present invention.

FIG. 4 is a flowchart of a method of providing multi spectral Doppler images, according to an embodiment of the present invention.

Referring to FIG. 4, the method according to the present embodiment includes time-series operations performed by the apparatus 300 of FIG. 3. Thus, although omitted, the detailed description about the apparatus 300 of FIG. 3 may also be applied to the method shown in FIG. 4.

As shown in FIG. 4, the apparatus 300 may display an ultrasound image of an object in the first region [S410]. In this case, the apparatus 300 may set a plurality of sample volumes in the displayed ultrasound image. According to an embodiment of the present invention, a plurality of sample volumes may be simultaneously set or may be set at a frequency corresponding to a predetermined period of time.

According to an embodiment of the present invention, the apparatus 300 may obtain a plurality of Doppler signals corresponding to the set sample volumes [S430]. According to an embodiment of the present invention, a plurality of Doppler signals may each be an analog signal or data that is digital-signal processed.

The apparatus 300 may tridimensionally display multi spectral Doppler images that are generated based on the obtained Doppler signals in the second region [S440]. That is, according to an embodiment of the present invention, the apparatus 300 may not display multi spectral Doppler images in respective separate graphs but may tridimensionally display multi spectral Doppler images along at least one axis (e.g., a horizontal axis) in a single graph.

According to an embodiment of the present invention, multi spectral Doppler images may include a 3D Doppler image or a vector Doppler image.

The apparatus 300 may display many Doppler images in a limited area and may not have to reduce the size of an ultrasound image (e.g., a B mode image) in order to further display a Doppler image corresponding as many as possible sample volumes.

According to an embodiment of the present invention, the apparatus 300 may display the Doppler images in the form of a perspective view in a single graph.

Figure 7:
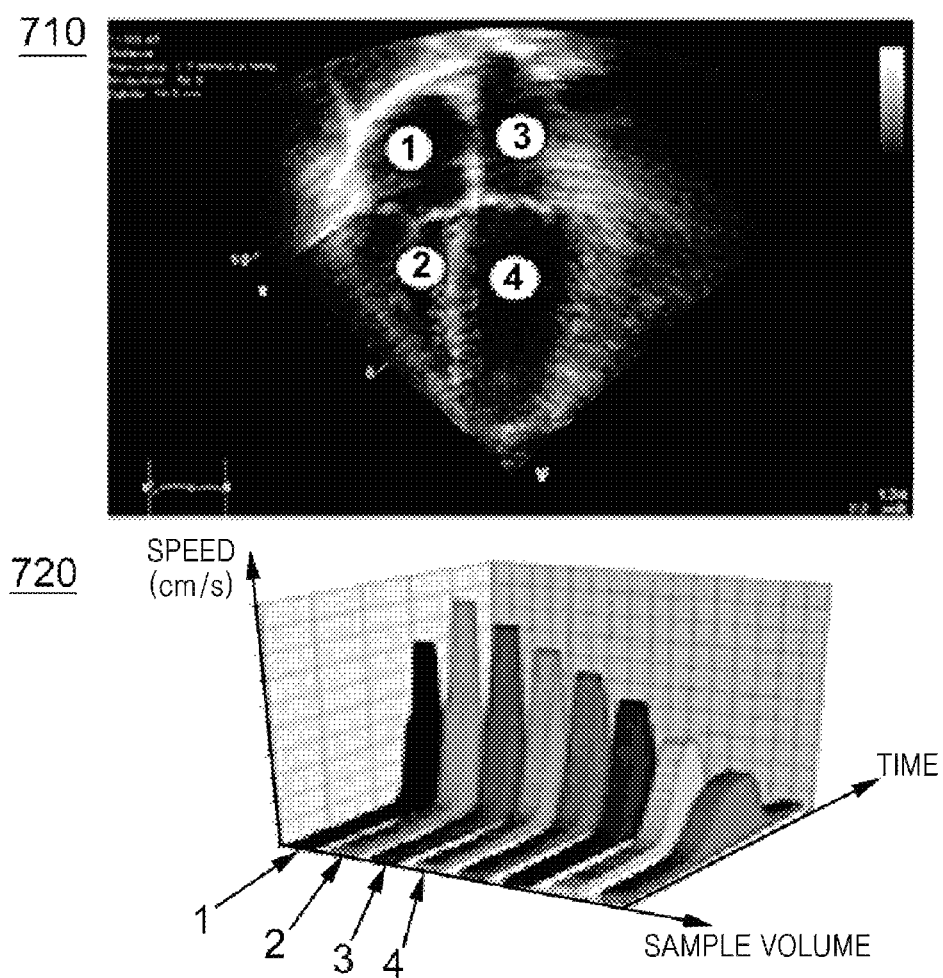
FIG. 7 is a diagram of a screen for providing multi spectral Doppler images, according to an embodiment of the present invention.

For example, as shown in FIG. 7, the apparatus 300 may display an ultrasound image in a first region 710. The apparatus 300 may display a Doppler image in a second region 720. In this case, the apparatus 300 may display multi spectral Doppler images 1, 2, and 3 corresponding to sample volumes ⌊, ⌊, and ⌊ along a single reference axis in a single sample volume. In FIG. 7, a graph in which multi spectral Doppler images are displayed has a speed axis, a sample volume axis, and a time axis. A reference axis is the sample volume axis.

When a sample volume ⌊ is further set in the ultrasound image displayed on the first region 710, the apparatus 300 may further display a Doppler image 4 corresponding to the sample volume ⌊ in a single graph.

As shown in FIG. 7, multi spectral Doppler images may each be a 3D Doppler image. The apparatus 300 may rotate the 3D Doppler images by 360 degrees and may display the rotated 3D Doppler images.

Figure 8:
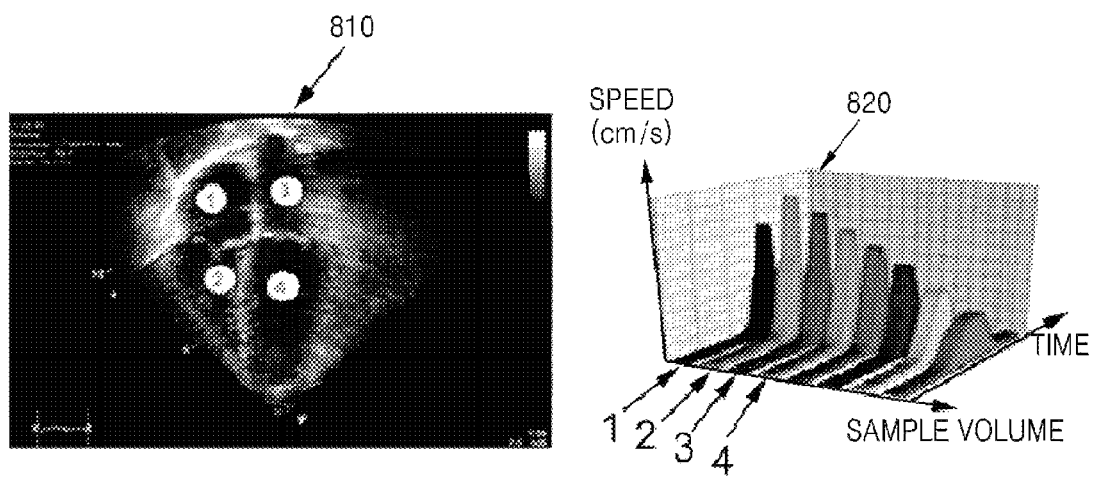
FIG. 8 is a diagram of a screen for providing multi spectral Doppler images, according to another embodiment of the present invention.

According to an embodiment of the present invention, the apparatus 300 may change positions of the first region for displaying the ultrasound image and the second region for displaying the Doppler image. For example, as shown in FIG. 7, in the apparatus 300, the first region 710 and the second region 720 may be vertically arranged. Alternatively, as shown in FIG. 8, a first region 810 and a second region 820 may be horizontally arranged.

Figure 5:
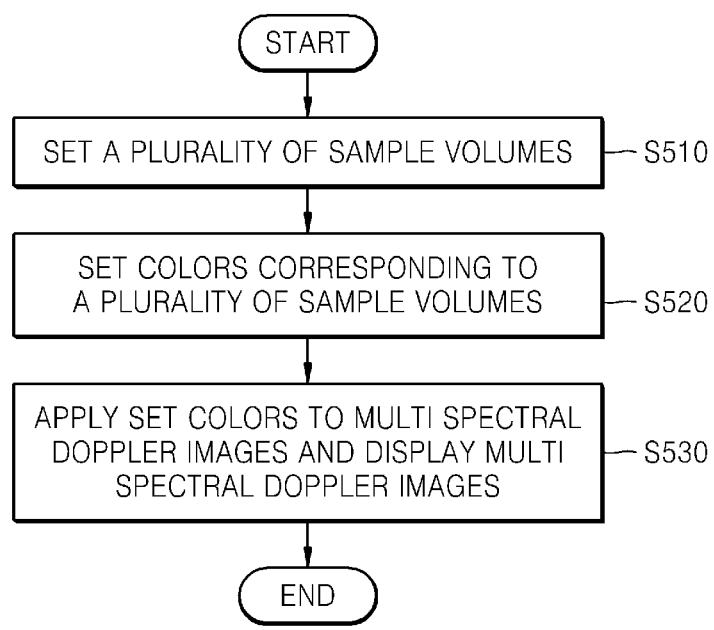
FIG. 5 is a flowchart of a method of mapping multi spectral Doppler images to colors, according to an embodiment of the present invention.

FIG. 5 is a flowchart of a method of mapping multi spectral Doppler images to colors, according to an embodiment of the present invention.

As shown in FIG. 5, in operation S510, the apparatus 300 may set a plurality of sample volumes in an ultrasound image of an object. In this case, in operation S520, the apparatus 300 may set colors corresponding to the set sample volumes.

For example, the apparatus 300 may map a black color to a first sample volume, may map a red color to a second sample volume, may map a blue color to a third sample volume, and may map a green color to a fourth sample volume.

In operation S530, the apparatus 300 may apply the set colors to multi spectral Doppler images and may display the Doppler images.

For example, as shown in FIG. 7, the apparatus 300 may display a Doppler image corresponding to the first sample volume as a black color, may display a Doppler image corresponding to the second sample volume as a red color, may display a Doppler image corresponding to the third sample volume as a blue color, and may display a Doppler image corresponding to the fourth sample volume as a green color.

Thus, according to an embodiment of the present invention, the apparatus 300 may allow a user to intuitively and easily distinguish multi spectral Doppler images corresponding to respective sample volumes.

Figure 6:
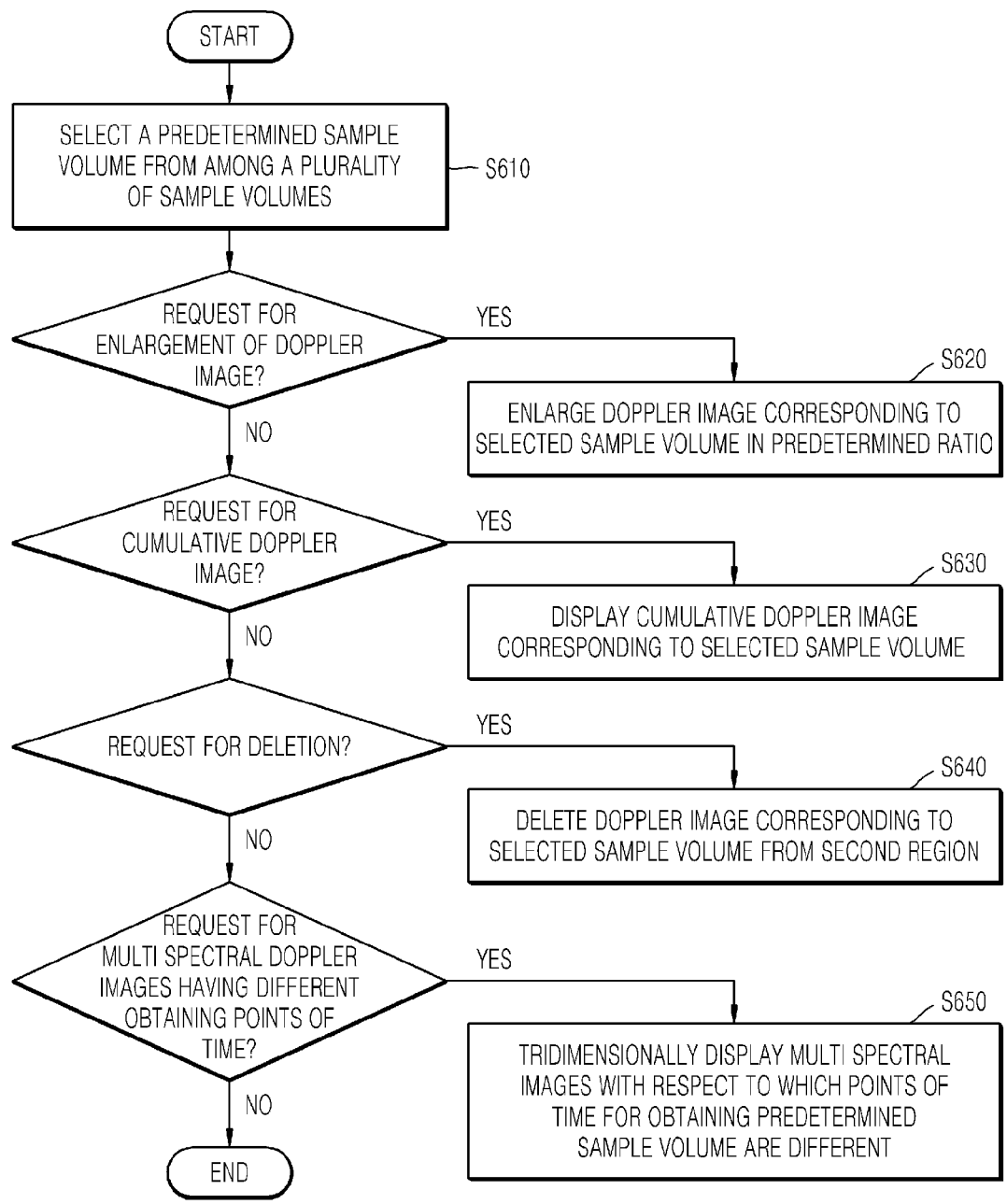
FIG. 6 is a flowchart of a method of providing multi spectral Doppler images, according to another embodiment of the present invention.

FIG. 6 is a flowchart of a method of providing multi spectral Doppler images, according to another embodiment of the present invention.

As shown in FIG. 6, according to an embodiment of the present invention, the apparatus 300 may select a predetermined sample volume from among a plurality of sample volumes [S610]. According to an embodiment of the present invention, the apparatus 300 may select a predetermined sample volume according to a user's input.

According to an embodiment of the present invention, when the apparatus 300 receives a request for enlargement of a Doppler image corresponding to the selected sample volume, the apparatus 300 may enlarge the Doppler image corresponding to the selected sample volume in a predetermined ratio and may display the Doppler image [S620].

According to another embodiment of the present invention, the apparatus 300 may emphasize only the Doppler image corresponding to the selected sample volume and may display the Doppler image or may display on the Doppler image corresponding to the selected sample volume.

According to an embodiment of the present invention, when the apparatus 300 receives a cumulative Doppler image of the selected sample volume, the apparatus 300 may display the cumulative Doppler image corresponding to the selected sample volume [S630]. Thus, according to an embodiment of the present invention, the apparatus 300 may allow a user to clearly compare and analyze changes in blood flow for a predetermined period of time in a set position (sample volume).

According to an embodiment of the present invention, when the apparatus 300 receives a request for deletion of the selected sample volume, the apparatus 300 may delete the Doppler image corresponding to the selected sample volume from the second region [S640].

For example, referring to FIG. 7, when the sample volume ⌊ is deleted from the ultrasound image displayed in the first region 710, the apparatus 300 may delete Doppler 4 corresponding to the deleted sample volume ⌊ from the second region 720.

According to an embodiment of the present invention, the apparatus 300 may tridimensionally display multi spectral Doppler images with respect to which points of time for obtaining a predetermined sample volume are different [S650].

Figure 9:
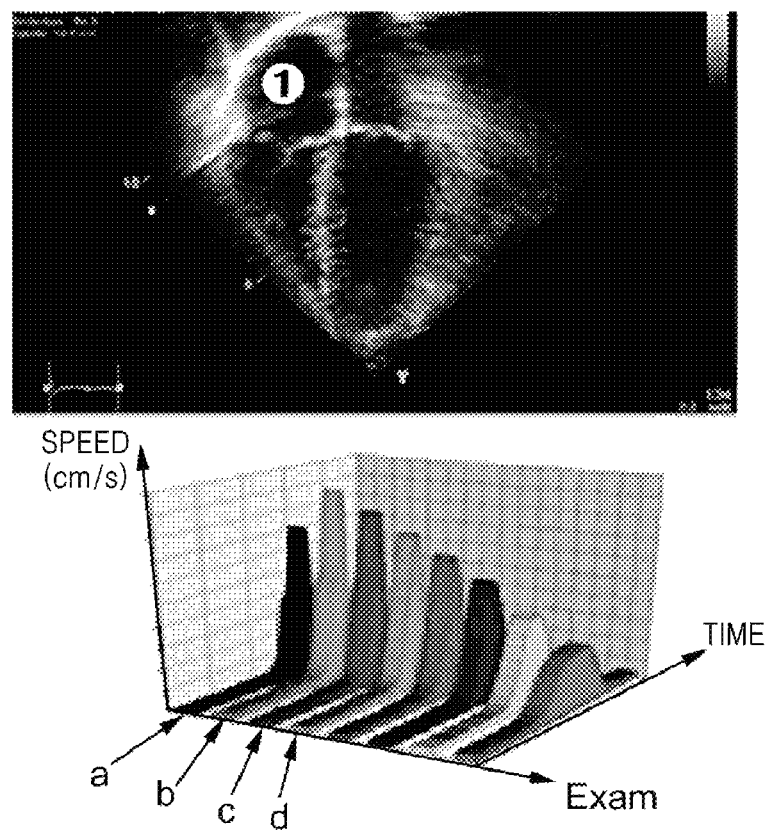
FIG. 9 is a diagram of a screen for providing multi spectral Doppler images with respect to which points of time for obtaining a predetermined sample volumes are different, according to an embodiment of the present invention.

For example, as shown in FIG. 9, the apparatus 300 may tridimensionally display in the second region Doppler images a, b, c, and d with respect to which points of time for obtaining the sample volume ⌊ are different. Accordingly, according to an embodiment of the present invention, a user may easily compare changes in Doppler images according to time in a predetermined sample volume.

Figure 10:
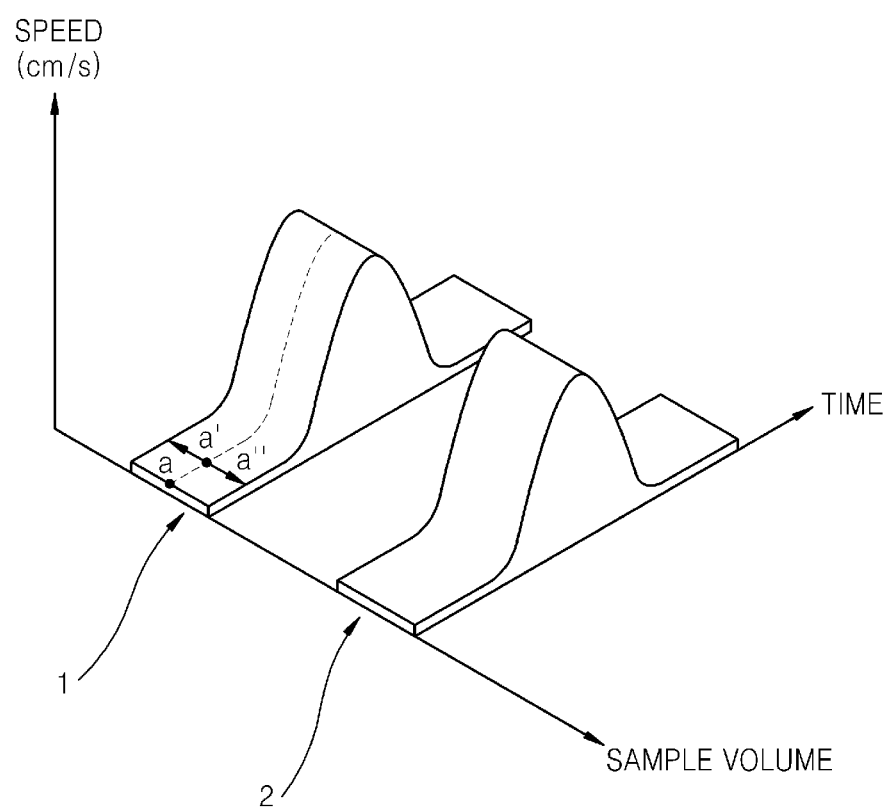
FIG. 10 is a diagram for showing a screen for displaying a plurality of vector Doppler images, according to an embodiment of the present invention.

FIG. 10 is a diagram for showing a screen for displaying a plurality of vector Doppler images, according to an embodiment of the present invention.

As shown in FIG. 10, the apparatus 300 may obtain a vector Doppler image corresponding to a sample volume. The vector Doppler image may include an amplitude and direction of speed of blood flow.

According to an embodiment of the present invention, the apparatus 300 may indicate the amplitude of the speed of blood flow as a line width in the vector Doppler image and may indicate the direction of the speed in right and left directions based on a central point. For example, when blood flows toward a probe, the apparatus 300 displays the direction as a left direction a' based on a central point a. In addition, when blood flows away from the probe, the apparatus 300 displays the direction as a right direction a" based on the central point a.

According to an embodiment of the present invention, the apparatus 300 may obtain at least one of elastic data and an ultrasound echo signal, which correspond to a plurality of sample volumes and may tridimensionally display in the second region at least one of a plurality of elastic images and a plurality of M mode images based on the obtained elastic data and ultrasound echo signal, which will be described with reference to FIG. 11.

Figure 11:
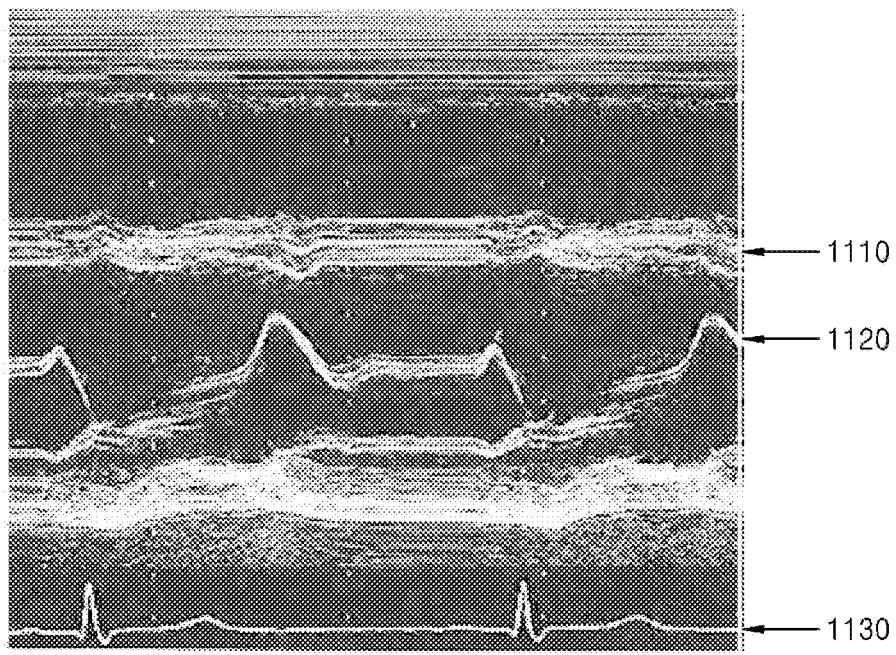
FIG. 11 is a diagram of a motion mode (M mode) image, according to an embodiment of the present invention.

FIG. 11 is a diagram of an M mode image, according to an embodiment of the present invention.

In the M mode image shown in FIG. 11, a vertical axis indicates a depth value and a horizontal axis indicates a time axis. That is, the M mode image is obtained by indicating as brightness amplitudes of ultrasound echo signals that are collected with respect to a single scan line at a frequency corresponding to a predetermined period of time.

Thus, there is no motion of an organ, the M mode image has a shape of parallel lines that are horizontally arranged in parallel to each other (1110). When there is motion of an organ, the M mod image has a wave pattern. In this case, an inclination of the wave pattern is proportional to a speed of motion of the organ. A lowermost image 1130 of the M mode image indicates electrocardiogram (ECG) waveform.

According to an embodiment of the present invention, a plurality of M mode images are tridimensionally displayed in a single graph and thus a user may compare and view motions of organs in a plurality of sample volumes.

The invention can also be embodied as programmed commands to be executed in various computer means, and then can be recorded to a computer-readable recording medium. The computer-readable recording medium may include one or more of the programmed commands, data files, data structures, or the like. The programmed commands recorded to the computer-readable recording medium may be particularly designed or configured for the invention or may be well known to one of ordinary skill in the art. Examples of the computer-readable recording medium include magnetic media including hard disks, magnetic tapes, and floppy disks, optical media including CD-ROMs, and DVDs, magneto-optical media including floptical disks, and a hardware apparatus designed to store and execute the programmed commands in read-only memory (ROM), random-access memory (RAM), flash memories, and the like. Examples of the programmed commands include not only machine codes generated by a compiler but also include great codes to be executed in a computer by using an interpreter.

According to an embodiment of the present invention, multi spectral Doppler images are tridimensionally displayed in a single graph, thereby effectively providing multi spectral Doppler images to a user. That is, according to an embodiment of the present invention, since an ultrasound image (e.g., a B mode image) and a Doppler image may be displayed in a predetermined region (screen) regardless of the number of sample volumes, user's view may not be dispersed and may easily compare an ultrasound image (e.g., a B mode image) and a Doppler image.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of providing multi spectral Doppler images, the method comprising:
    displaying an ultrasound image of an object in a first region;
    setting a plurality of sample volumes in the displayed ultrasound image;
    obtaining a plurality of Doppler signals corresponding to the plurality of sample volumes; and
    tridimensionally displaying in a second region the multi spectral Doppler images that are generated based on the plurality of Doppler signals according to a z-axis of a 3D coordinate system having a x-axis, a y-axis, and the z-axis,
    wherein the multi spectral Doppler images include a first Doppler image selected, based on at a first point of time from a Doppler image corresponding to a sample volume from among the plurality of sample volumes and a second Doppler image selected, based on at a second point of time different from the first point of time, from the Doppler image, and
    wherein the first Doppler image and the second Doppler image are displayed at different positions of the z-axis of the 3D coordinate system.

2. The method of claim 1, wherein the displaying comprises displaying the multi spectral Doppler images in the form of a perspective view in a single graph.

3. The method of claim 1, wherein the multi spectral Doppler images comprises a plurality of vector Doppler images.

4. The method of claim 1, further comprising:
    setting colors corresponding to the plurality of sample volumes; and
    applying the set colors to the multi spectral Doppler images and displaying the multi spectral Doppler images.

5. The method of claim 1, further comprising:
    further setting a sample volume to the displayed ultrasound image; and
    further and tridimensionally displaying a Doppler image corresponding to a further set sample volume in the second region.

6. The method of claim 1, further comprising:
    deleting a sample volume from the displayed ultrasound image; and
    deleting a Doppler image corresponding to the deleted sample volume from the second region.

7. The method of claim 1, wherein the displaying comprises rotating the multi spectral Doppler images by 360 degrees and displaying the multi spectral Doppler images.

8. The method of claim 1, further comprising:
    obtaining a cumulative Doppler image indicating a change in blood flow for a predetermined period of time corresponding to at least one sample volume from among a plurality of sample volumes; and displaying the cumulative Doppler image in the second region.

9. The method of claim 1, further comprising:
obtaining elastic data corresponding to the plurality of sample volumes; and
tridimensionally displaying in the second region a plurality of elastic images based on the elastic data.

10. The method of claim 1, further comprising:
obtaining an ultrasound echo signal corresponding to the plurality of sample volumes; and
tridimensionally displaying in the second region a plurality of motion mode (M mode) images based on the ultrasound echo signal.

11. A non-transitory computer readable recording medium having recorded thereon a program for executing the method of claim 1.

12. An apparatus for providing multi spectral Doppler images, the apparatus comprising:
an image processor configured to set a plurality of sample volumes in a displayed ultrasound image;
an obtainer configured to obtain a plurality of Doppler signals corresponding to the plurality of sample volumes;
a display configured to display an ultrasound image of an object in a first region and tridimensionally display in a second region the multi spectral Doppler images that are generated based on the plurality of Doppler signals according to a z-axis of a 3D coordinate system having a x-axis, a y-axis, and the z-axis; and
a controller configured to control the image processor, the obtainer, and the display,
wherein the multi spectral Doppler images include a first Doppler image selected, based on at a first point of time from a Doppler image corresponding to a sample volume from among the plurality of sample volumes and a second Doppler image selected, based on at a second point of time different from the first point of time, from the Doppler image, and
wherein the first Doppler image and the second Doppler image are displayed at different positions of the z-axis of the 3D coordinate system.

13. The apparatus of claim 12, wherein the display displays the multi spectral Doppler images in the form of a perspective view in a single graph.

14. The apparatus of claim 12, wherein the multi spectral Doppler images comprises a plurality of vector Doppler images.

15. The apparatus of claim 12, wherein the image processor sets colors corresponding to the plurality of sample volumes, and
wherein the display applies the set colors to the multi spectral Doppler images and displays the multi spectral Doppler images.

16. The apparatus of claim 12, wherein the image processor further sets a sample volume to the displayed ultrasound image, and
wherein the display tridimensionally displays a Doppler image corresponding to a further set sample volume in the second region.

17. The apparatus of claim 12, wherein the image processor deletes a sample volume from the displayed ultrasound image, and
wherein the display deletes a Doppler image corresponding to the deleted sample volume from the second region.

18. The apparatus of claim 12, wherein the display rotates the multi spectral Doppler images by 360 degrees and displays the multi spectral Doppler images.

19. The apparatus of claim 12, wherein the obtainer obtains a cumulative Doppler image indicating a change in blood flow for a predetermined period of time corresponding to at least one sample volume from among a plurality of sample volumes, and
wherein the display displays the cumulative Doppler image in the second region.

20. The apparatus of claim 12, wherein the obtainer obtains elastic data corresponding to the plurality of sample volumes, and
wherein the display tridimensionally displays in the second region a plurality of elastic images based on the elastic data.

21. The apparatus of claim 12, wherein the obtainer obtains an ultrasound echo signal corresponding to the set plurality of sample volumes, and
wherein the display tridimensionally displays in the second region a plurality of motion mode (M mode) images based on the obtained ultrasound echo signal.

* * * * *